United States Patent [19]

Fraser

[11] 3,996,010
[45] Dec. 7, 1976

[54] BREATHING GAS ANALYZER

[75] Inventor: Robert B. Fraser, El Cerrito, Calif.

[73] Assignee: Searle Cardio-Pulmonary Systems Inc., Emeryville, Calif.

[22] Filed: Mar. 25, 1976

[21] Appl. No.: 670,127

Related U.S. Application Data

[63] Continuation-in-part of Ser. No. 528,089, Nov. 29, 1974, Pat. No. 3,951,607.

[52] U.S. Cl. .............................. 23/254 E; 356/178; 250/226; 250/576; 313/217; 313/218
[51] Int. Cl.² ................... G01J 3/50; G01N 21/26; G01N 33/16; H01I 5/16
[58] Field of Search ......... 23/254 E, 254 R, 255 E, 23/255 R, 232 E, 232 R; 356/187, 178; 250/226, 564, 573, 575, 576; 313/217, 218

[56] References Cited

UNITED STATES PATENTS

3,951,607  4/1976  Fraser .............................. 23/254 E

*Primary Examiner*—Robert M. Reese
*Attorney, Agent, or Firm*—Lothrop & West

[57] ABSTRACT

A breathing gas analyzer, especially for pulmonary use, has a frame supporting a centrally mounted radiation or analyzing chamber of about 1 and one-half to 25 millimeters (0.06 to 1.0 inches) substantially uniform inside diameter, having a circular-cylindrical transparent wall with closed ends connected in an electrical circuit and providing an anode of brass or stainless steel and a cathode of tantalum and constituting a discharge tube. Leading from a patient's breathing tube is a conduit passing axially through the cathode, the conduit having an inside diameter of about 0.03 to 0.25 inches (0.7 to 6.4 millimeters). The chamber is subjected to subatmospheric pressure of about 0.2 to 10.0 torr through a duct from about one thirty-second to one-quarter inches (0.8 to 6.4 millimeters) inside diameter, passing through the anode to a vacuum pump. Arrayed equidistantly from the axis and around the chamber are one or more radiation detection devices positioned opposite the negative glow region of the discharge. The detection devices may be connected to a display device. There are individual apertures and filters interposed between the chamber and each of the detecting devices.

7 Claims, 17 Drawing Figures

BREATHING GAS ANALYZER

This application is a continuation-in-part of application Ser. No. 528,089 filed Nov. 29, 1974 now U.S. Pat. No. 3,951,607.

The present gas analyzer is constructed to show the presence of any one or more of a relatively large number of various breathing gases as they may be found in a patient's breathing tract and evidenced in the negative glow region of a discharge tube, individual gases being identified by their characteristics discerned through appropriate viewing and filtering devices.

In the medical field there is an increasing need for a simple, portable, accurate and reliable means for determining one or more gas constituents in a patient's breath and for detecting relatively small amounts of physiological gases and anaesthetic gases in a breathing tube connected to a patient. Heretofore it has seemed advisable to utilize a special, single gas as a means for energizing or triggering the response of such a mechanism to others of the gases present, but preferably the present arrangement utilizes no extra or carrier or trigger gas in order to afford an adequate indication of numerous gases present in a patient's breath.

There is a requirement for determining the presence of a number of different gases exhaled by a patient through a breathing tube, perhaps five or six being the customary number of interest, although more or less can be detected when desired.

It is therefore an object of the invention to provide an improved gas analyzer that is sufficiently light and simple as to be portable, that is sufficiently accurate and straightforward as to operate well over a protracted period and that is especially sharp in detecting each of a relatively large number of breathing gases.

Another object of the invention is to provide a gas analyzer that quickly furnishes a reliable indication of the presence in a patient's breath of any one or more of several different gases of physiological interest.

A further object of the invention is to provide a gas analyzer that can be generally utilized without a special, energizing gas.

An additional object of the invention is to provide a gas analyzer in which the various size or dimensional characteristics and preferred operating conditions and values are such as to produce a quick response time and good stability without sacrificing accuracy.

Another object of the invention is to provide a generally improved breathing gas analyzer.

Other objects, together with the foregoing, are attained in the embodiment of the invention described in the accompanying description and illustrated in the accompanying drawings, in which:

Figure 1:
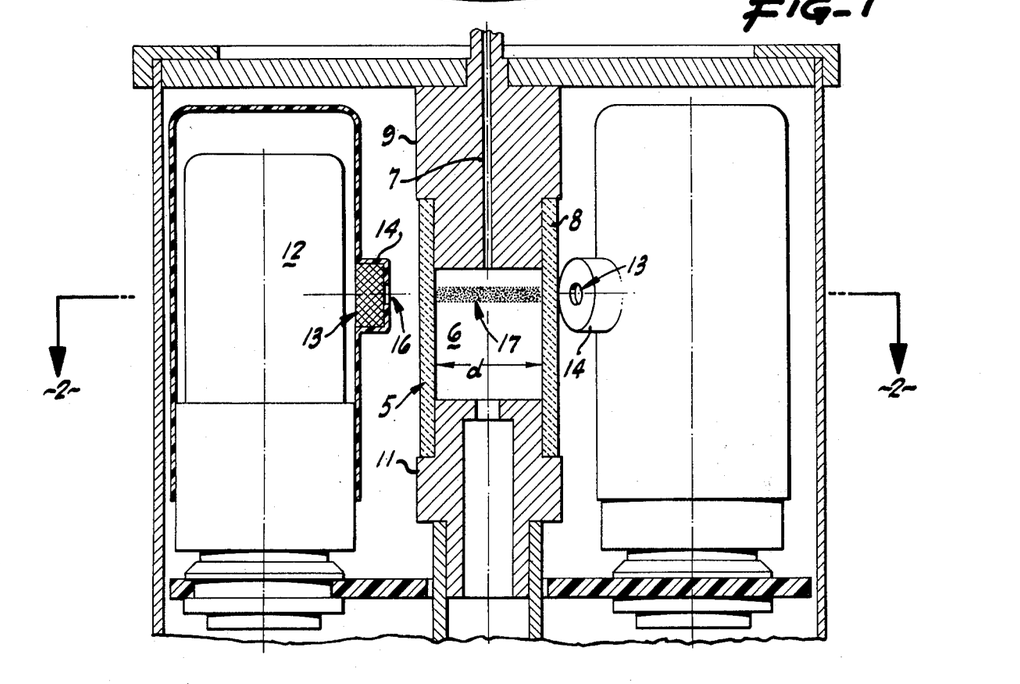
FIG. 1 is a diagrammatic view, generally on an axial plane, of one portion of a gas analyzer constructed pursuant to the invention.
Figure 2:
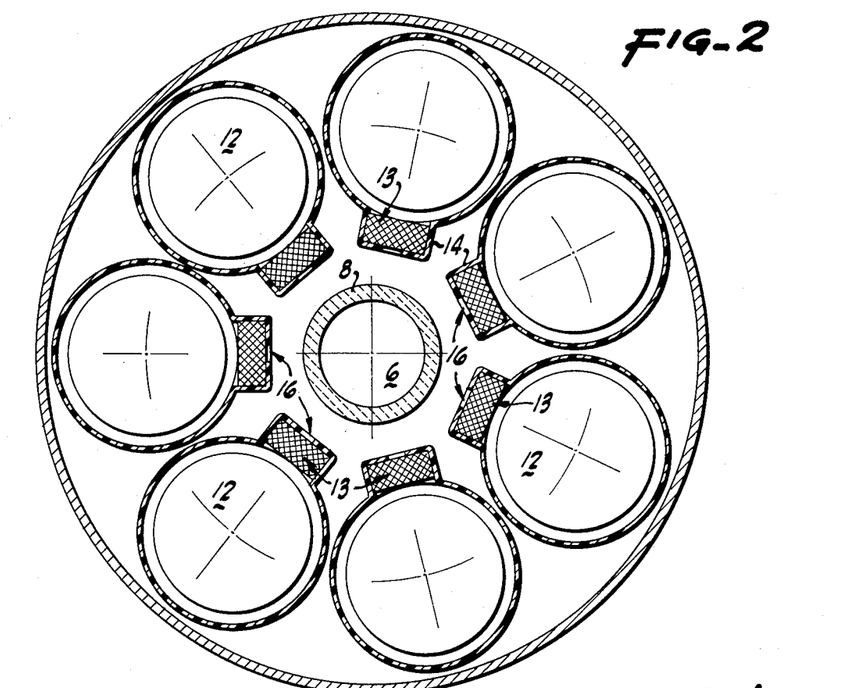
FIG. 2 is a cross-section, portions being broken away, through the analyzer of FIG. 1, the plane of section being indicated by the line 2—2 of FIG. 1.

The breathing gas analyzer accurately measures the concentrations in a patient's breath of respiratory gases, gases used in pulmonary function measurements and anaesthetic gases. As shown in FIGS. 1 and 2, there is provided a radiation or analyzing or discharge chamber 5 in which is produced a plasma 6 of the gas being sampled. Such gas is supplied from a patient's breathing tube to the chamber through a sampling tube 7 of a diameter of 0.03 to 0.25 inches. The chamber 5, having a diameter $d$ in the range of about 0.06 inches to 1 inch, is defined by a transparent tube such as a quartz or "Pyrex" tube 8 having metal electrodes 9 and 11 disposed at opposite ends. To minimize sputtering and oxidation, the cathode electrode 9 is tantalum and the anode electrode 11 is of brass or stainless steel. The plasma 6 or stable glow discharge is established by applying an electrical potential across the electrodes 9 and 11 using a constant current supply set to deliver between 0.1 and 5.0 milliamperes. The chamber 5 is operated at a constant pressure within a range of about 0.2 to 10.0 torr maintained by a vacuum pump (not shown) connected to the chamber through a duct in the anode 11 of from 0.03 to 0.25 inches in diameter. The gas flow rate through the chamber is about 2.0 to 50.0 cc/minute.

Certain spectral lines or bands corresponding to the gas components of interest are effective on properly connected photomultiplier tubes 12 arranged around the chamber and connected to an appropriate display (not shown). Each chosen band is observed or extracted from the total emission of the glow discharge through a selected, thin-film interference filter 13 screened by a disc 14 having a small, pinhole aperture 16 opposite and receiving energy only from the immediate vicinity of the cathode, primarily from the negative glow region 17 of the chamber 5. In some instances, the apertured disc 14 is replaced or accompanied by an optical lens. The filters 13 pass half-power bands ranging in width from about 6 to 30 angstroms. The filters 13 have a spectral response that provides nearly a Gaussian profile in the region of interest and are open to some small radiation on either side of the chosen spectral band.

The radiant energy in the desired spectral band is detected by a separate one of the photomultiplier tubes 12 for each chosen gas. The photomultiplier tubes 12 and their special filters 13 are arranged around the discharge tube 8 with their respective disc apertures opposite to the negative glow region of the plasma 6 or in the negative glow "plane" so that several gases in a mixture can be detected and measured simultaneously or in rapid sequence.

The optimal operation current is determined by the maximum current which can be passed through the discharge tube and still maintain a stable negative glow region 17. The maximum current ($i_{d\max}$) consistent with stability is a function of the concentration of gas, the gas pressure, the chamber diameter, the electrode geometry and materials and the type or characteristics of the power supply (not shown) to the chamber.

Figure 3:
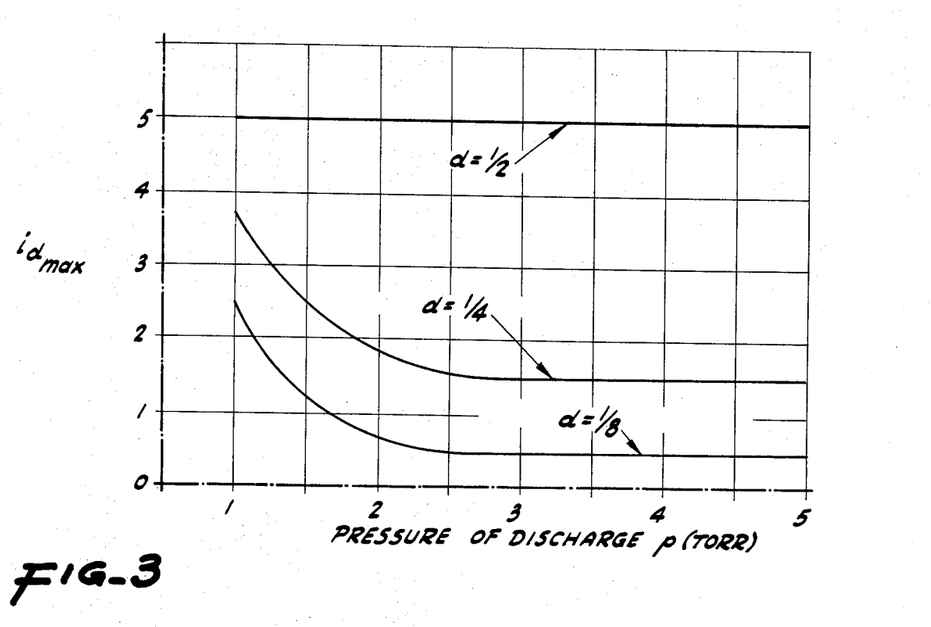
FIG. 3 is a graph showing the maximum current available with stable discharge for chambers of different diameters.

Some typical curves of maximum current in milliamperes plotted against discharge chamber pressure ($p$) are shown in FIG. 3 at a gas flow rate ($v$) of about 10 cc/minute. Preferably, operation for good stability is somewhat below maximum current. For a pressure ($p$) of 4 torr and a chamber diameter of one-quarter inch, this is about 1.5 milliamperes. A large stable current is chosen because the greater the current the greater the intensity of emission and hence the lower the signal to noise ratio.

Figure 4:
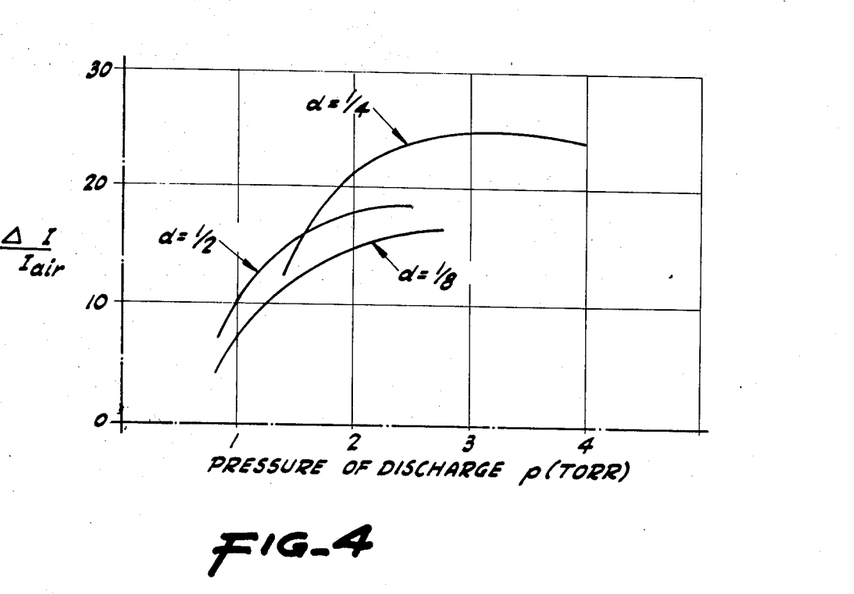
FIG. 4 is a graph showing change in current output with respect to variations in the pressure in the discharge chamber.

The optimal operating pressure and optimal discharge tube diameter are determined by choosing the particular pressure and particular diameter which give the greatest emission for the most critical breathing gas component, which is CO. Carbon monoxide cannot be present in pulmonary function mixtures, for health reasons, at concentrations greater than 0.3 percent. From FIG. 4, plotted from measurements of CO and showing pressure of discharge as abscissae and showing as ordinates in tenths of 1 percent the increase in intensity of emission due to the amount of CO present. From the relationship that $\Delta I$ equals $I_{CO} - I_{air}$, (wherein $I_{CO}$ is the intensity of emission of a gas mixture of 0.3% CO and the balance air, and $I_{air}$ is the intensity of emission of air without another gas) it is clear that the optimal diameter ($d$) for the tube 8 is close to one-quarter inch.

Figure 5:
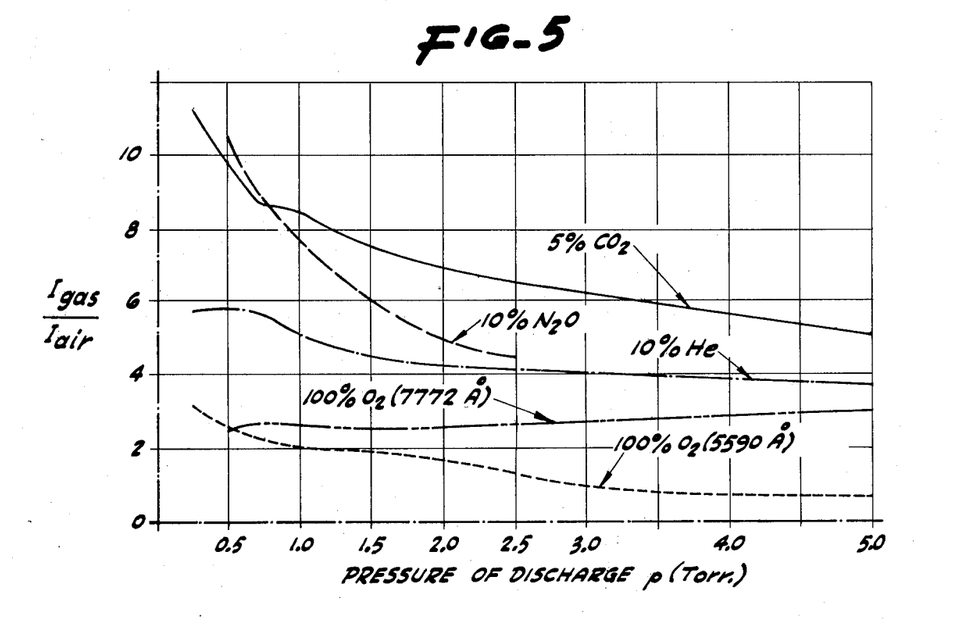
FIG. 5 is a graph showing the relationship of the currents corresponding to a number of different gases with respect to the current for air as a variation of the discharge pressure.

Since the discharge should operate below a pressure of about 6 torr for stability, the optimal pressure range as shown in FIG. 4 is about 2.5 torr to 5.0 torr. Comparable curves showing the intensity of emission for 5 percent $CO_2$, 10 percent $N_2O$, 10 percent He and two curves for 100 percent $O_2$ at 7772 angstroms and at 5590 angstroms are shown in FIG. 5. In this figure, the chamber tube diameter is one-quarter inch, the current is 1.0 milliamperes and the flow rate is 10 cc/minute. Within this pressure range there is not any great sacrifice with increasing pressure in relative emission intensities ($I_{gas}/I_{air}$) of the several gases shown. In fact, $O_2$ at 7772 angstroms even shows a slight increase in relative emission with increasing pressure and the other gases show only slight decreases.

Figure 6:
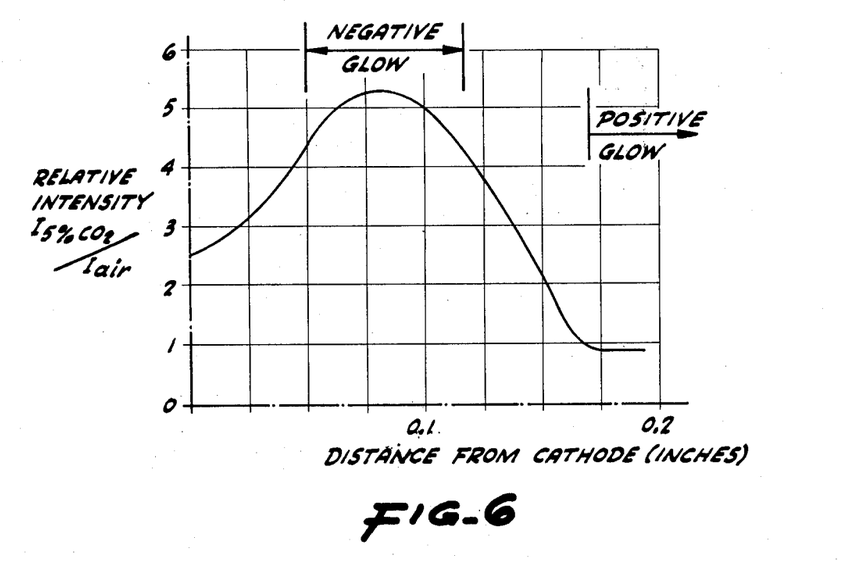
FIG. 6 is a graph showing the relationship of the relative current intensity of the discharge beam as the distance from the cathode is varied.
Figure 7:
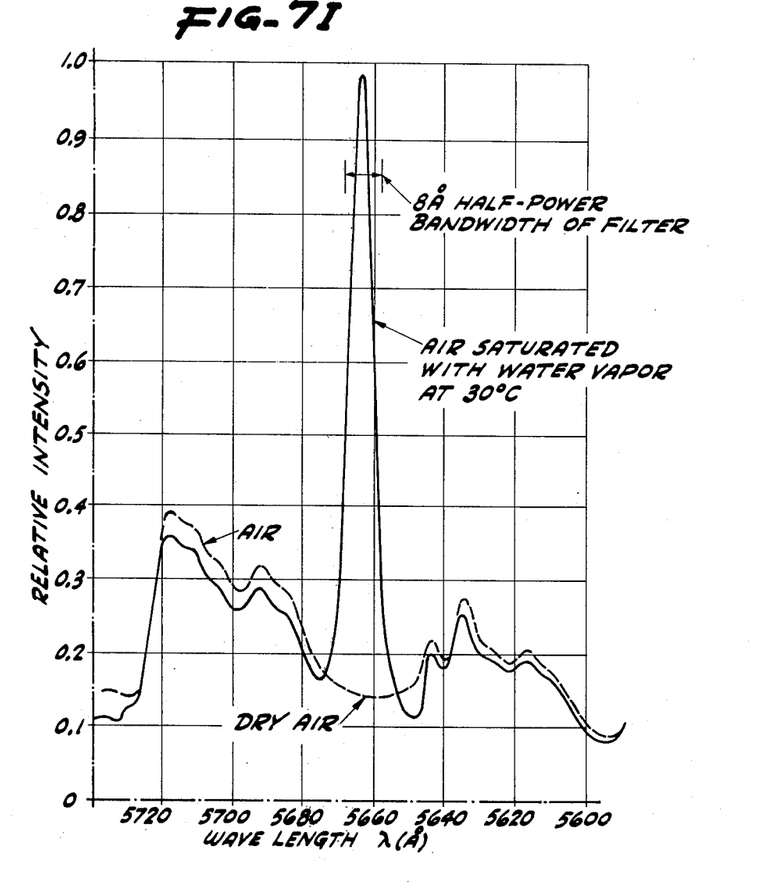
FIG. 7A is a graph of the relative intensity of the emission beam of air and of $O_2$ plotted with respect to a pertinent wave length band.
FIG. 7B is a graph similar to 7A but showing a curve for air alone at a different wave length region.
FIG. 7C is a similar graph showing the curves for 5 percent $CO_2$ in air.
FIG. 7D is a similar graph showing intensity of the beam current for 10 percent $N_2O$, the balance being air.
FIG. 7E is a similar graph showing the curve for 10 percent helium, the balance being air.
FIG. 7F is a similar graph showing the curve for 10 percent argon, the balance being air.
FIG. 7G is a similar graph for $N_2$, the balance being air, certain other gases such as 0.3 percent CO, argon and $O_2$ likewise being indicated.
FIG. 7H is a similar graph showing the relative intensity of 4.0 percent "halothane" and comparable anaesthetic gases.
FIG. 7I is a similar graph for air saturated with water vapor as well as for dry air.
Figure 7A:
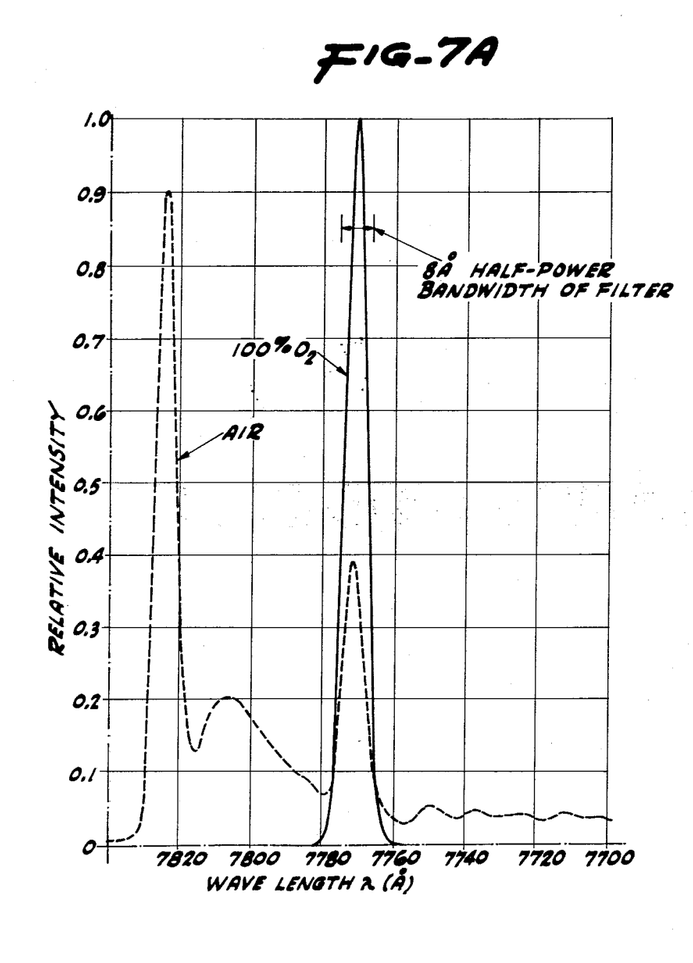
Figure 7B:
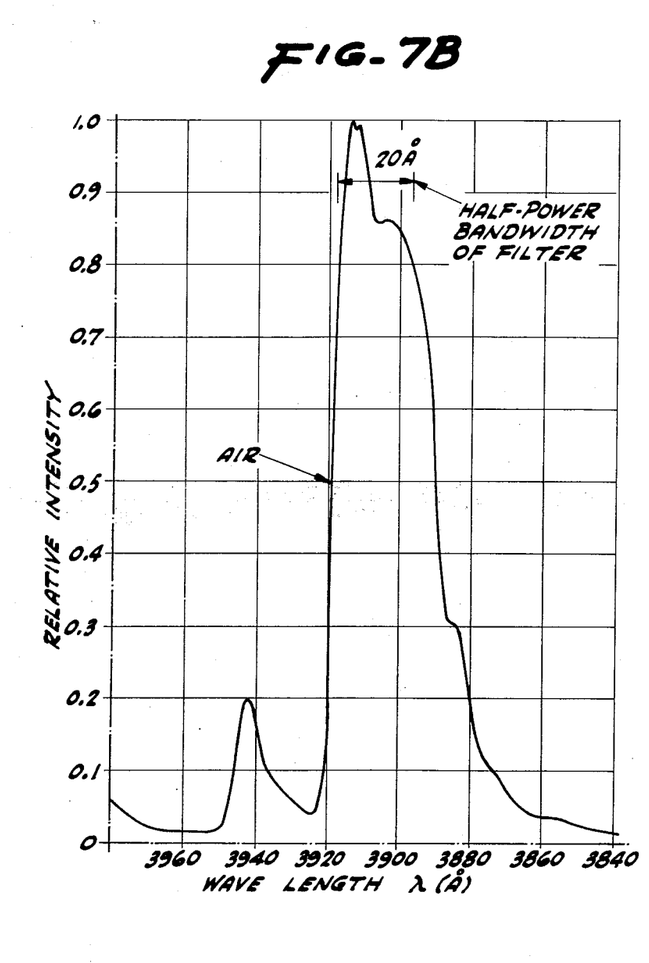
Figure 7C:
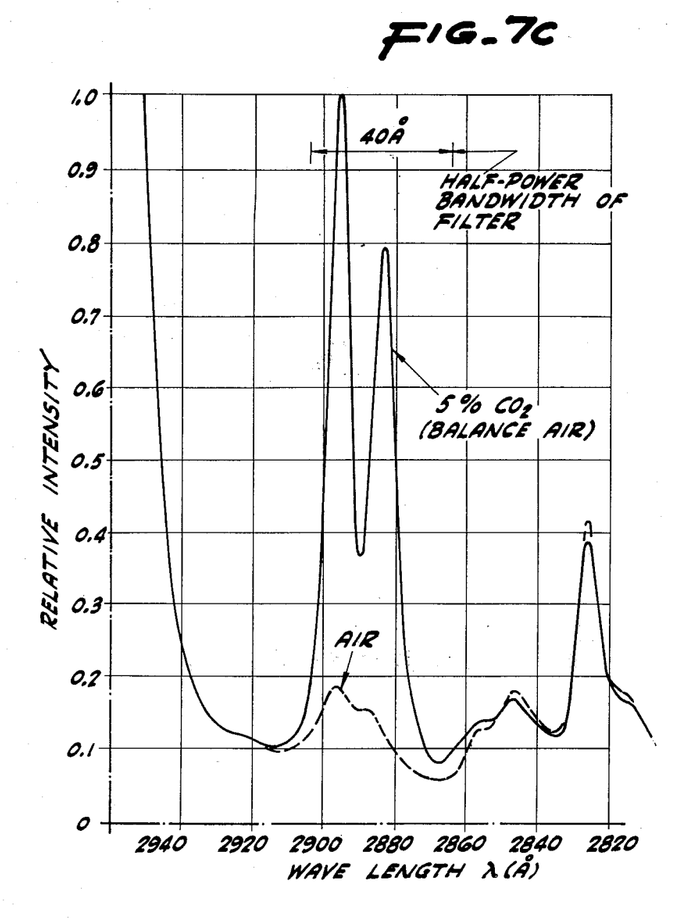
Figure 7D:
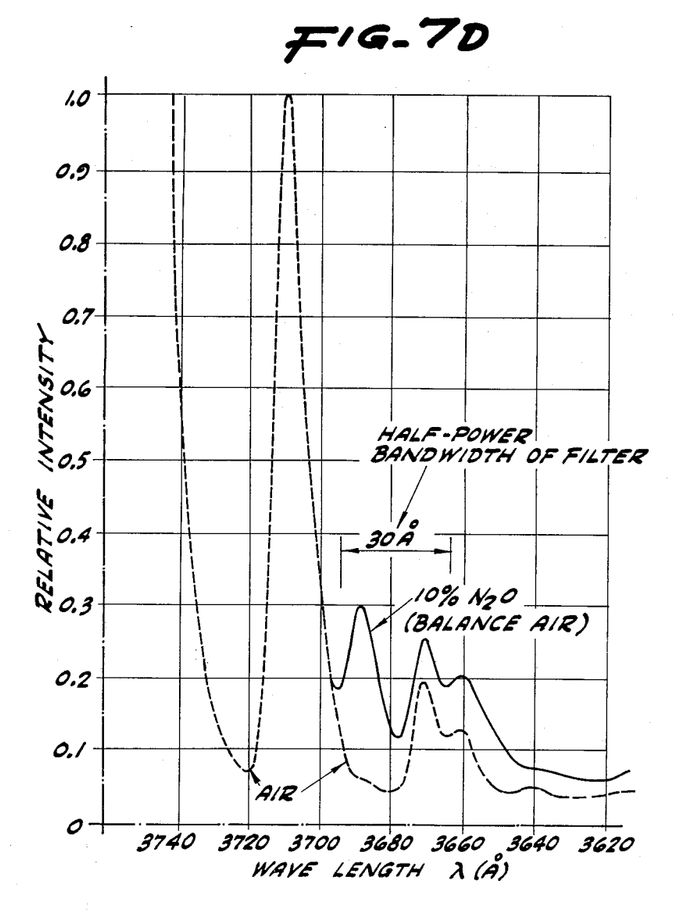
Figure 7E:
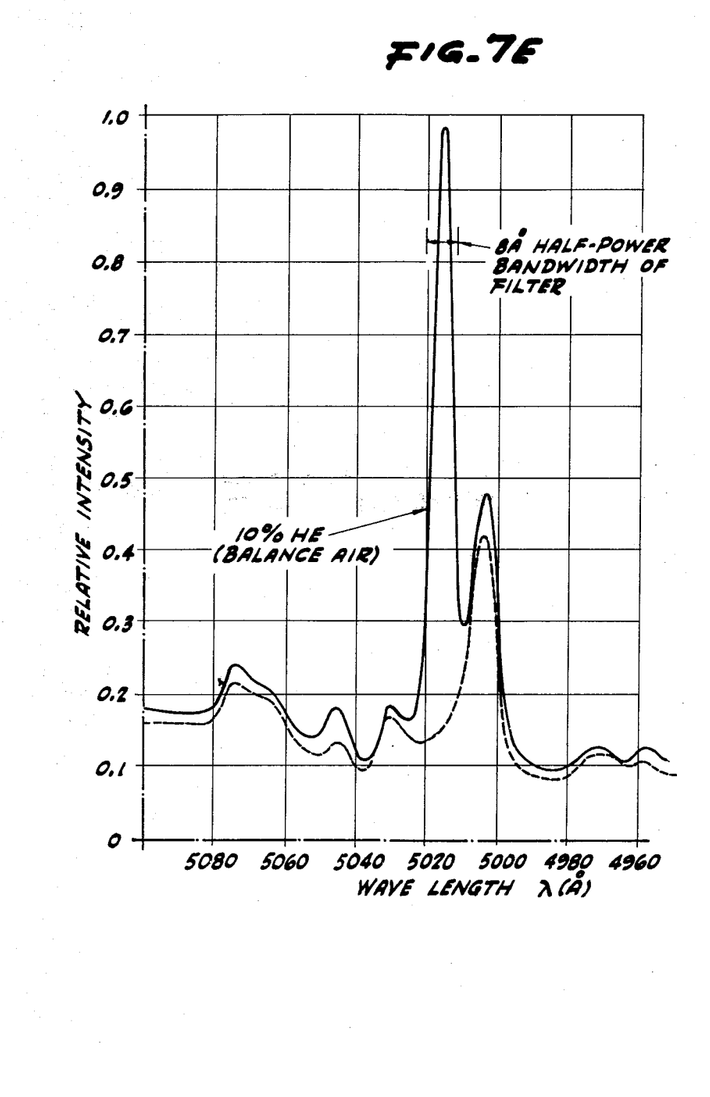
Figure 7F:
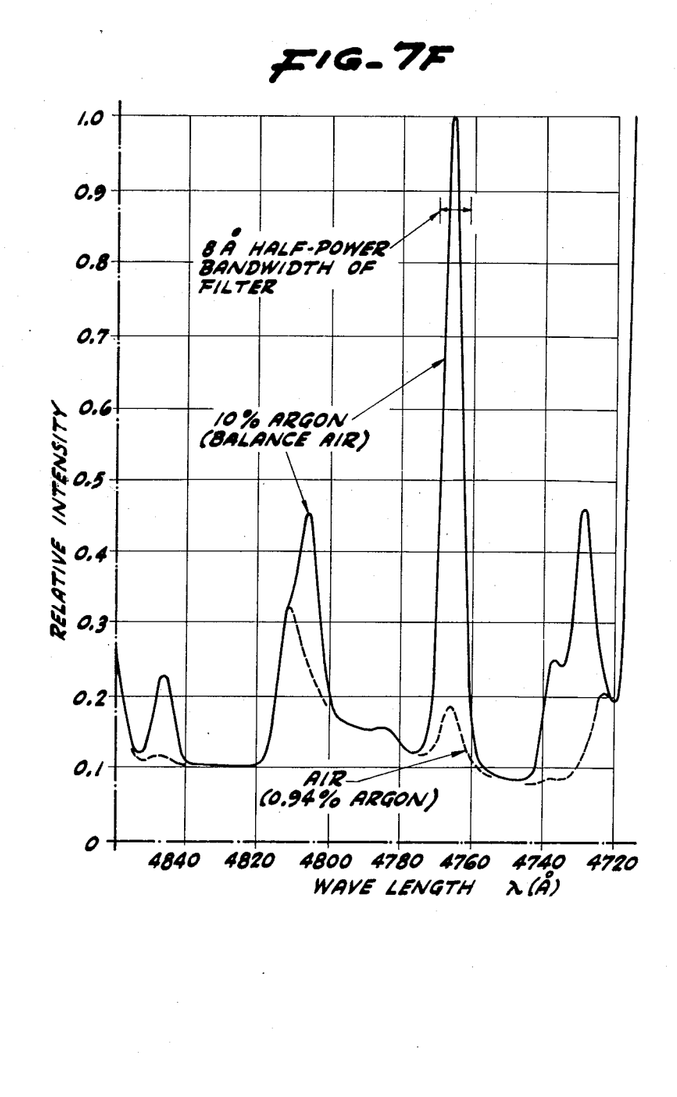
Figure 7G:
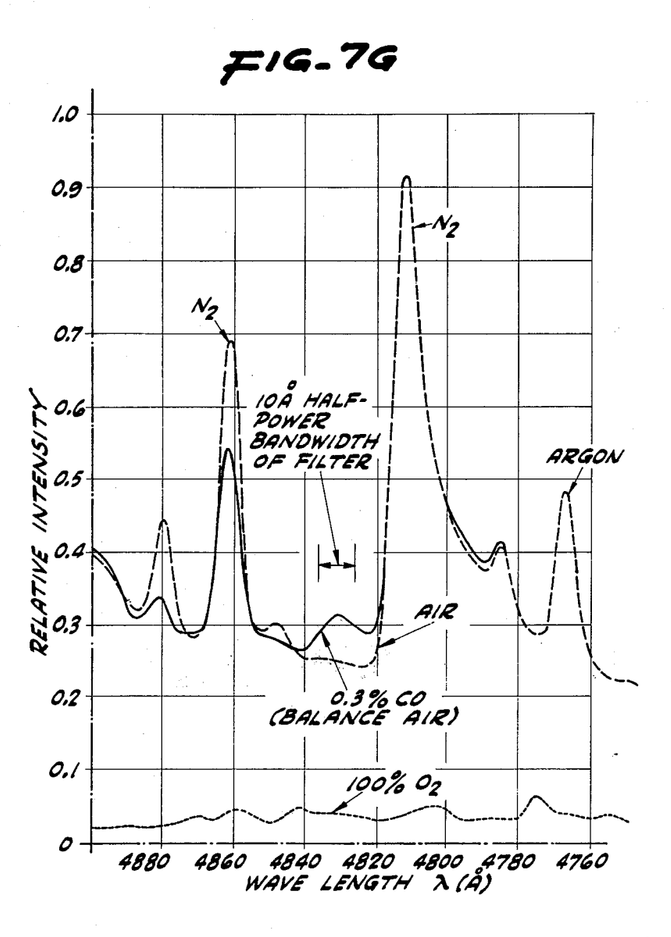
Figure 7H:
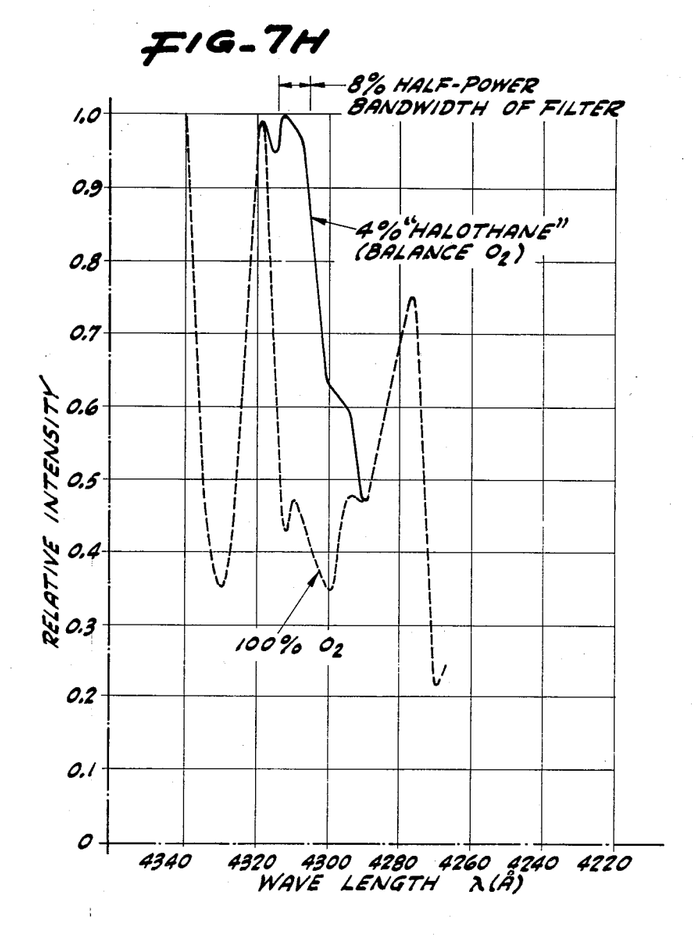

It is quite critical to determine the optimum point of observation of the glow discharge as a location along the axis of the discharge chamber 5. As shown in FIG. 6, the plot is of the relative intensity of the emission for 5 percent $CO_2$ in air as governed by the axial distance away from the cathode 9, expressed in inches. The optimal "viewing" or energy extraction position lies within the negative glow region 17 and lies very close to the cathode surface, a distance from that surface of about 0.25 to 0.05 inches for pressures from 0.3 to 5.0 torr and at a current of 1.0 milliamperes. While the scan or view may be from the cathode surface itself to the lower (in FIG. 1) reach of the negative glow region, the preferred position is at an intermediate distance, as shown. This is because the emission intensity ($I_{gas}/I_{air}$) of the discharge drops off rapidly in both directions away from the negative glow and particularly is less than unity in the positive glow region, since the gas present is not 100 percent air. While H, $O_2$, and $N_2$ can be detected in the positive glow, it is only in the negative glow that the presence of $CO_2$, $N_2O$, He, CO and some other gases may be discerned.

The optimal wavelength bands for the filters are chosen from a spectral survey of each gas passed through the discharge chamber. Examples of these relative intensity surveys for wavelength bands near and including the optimal are shown in FIGS. 7A through 7I. In all these figures, the chamber tube diameter is one-quarter inch, the pressure is 2.5 torr, the discharge current is 1.25 milliamperes and the flow rate is 10 cc/minute. The optimal spectral band of a particular gas is that one which has the least interference due to the other gases, especially air.

Figure 8A:
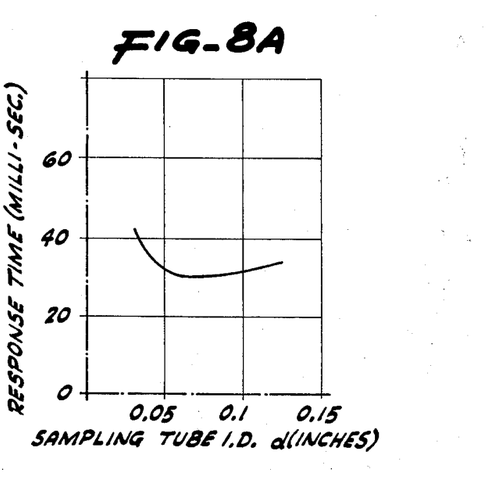
FIG. 8A is a graph showing response time in milliseconds at a pressure of 2 and one-half torr as it varies with sampling tube diameter changes.
Figure 8B:
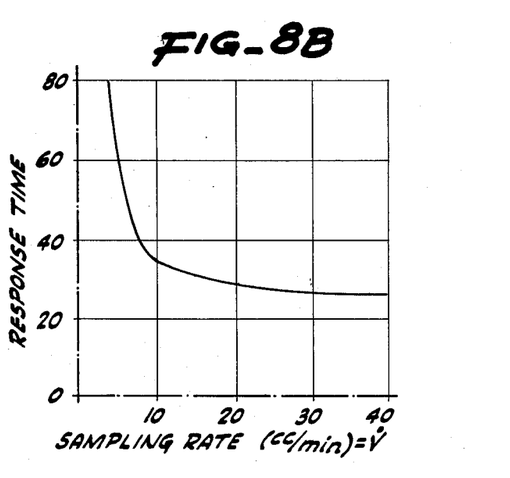
FIG. 8B is a graph showing response time against sampling rate for a sampling tube having a diameter of 0.06 inches.

The diameter ($d$) of the sampling tube has an effect on the response time of the instrument and has an optimal value of about one-sixteenth inch. As plotted in FIG. 8A the response time in milliseconds varies with the sampling tube diameter $d$ at a pressure of 2.5 torr and a flow rate of 9 cc/minute, the current being 1 milliampere. An optimum sampling tube diameter is about 0.06 inches or one-sixteenth inch. The response time also varies with the sampling rate ($v$) as plotted in FIG. 8B and as measured in milliseconds and cc/minute when the pressure is 2.5 torr and the sampling tube diameter is 0.06 inches. A sampling rate of 10 cc/minute or more is preferred under these conditions.

With this arrangement as described in operating within the ranges set forth, it is possible to derive quickly and accurately responsive curves for a number of gases discernable in the negative glow region in order to afford clear indications of numerous breathing gases.

What is claimed is:

1. A breathing gas analyzer especially for pulmonary use comprising a cylindrical analyzing chamber of transparent insulating material and of substantially uniform internal diameter of from about 0.06 to 1.0 inches between said ends, a cathode at one end of said chamber and having extending axially therethrough a conduit of a diameter of about 0.03 to 0.25 inches adapted to be connected to a source of breathing gas, an anode at the other end of said chamber and having extending axially therethrough a duct of a diameter of about 0.03 to 0.25 inches for connecting said chamber to a sub-atmospheric pressure and thereby draw gases from said conduit through said chamber and out said duct, means for applying to said cathode and said anode a voltage difference to cause radiation from gas in said chamber and establish a negative glow region in said chamber, a radiation detection device disposed alongside said chamber in a direct radiation path therefrom, means disposed in said path for limiting radiation on said device to radiation from said negative glow region, and a radiation filter in said path adapted to transmit primarily radiation from a selected gas in said negative glow region.

2. An analyzer as in claim 1 in which said radiation limiting means is an apertured disc.

3. An analyzer as in claim 1 in which said radiation limiting means is a lens.

4. An analyzer as in claim 1 in which the operating pressure in said analyzing chamber ranges from about 0.2 torr to 10.0 torr.

5. An analyzer as in claim 1 in which the gas flow rate through said analyzing chamber is about 2.0 to 50.0 cc/minute.

6. An analyzer as in claim 1 in which the current for a one-quarter inch diameter analyzing chamber is about 0.3 to 1.5 milliamperes.

7. An analyzer as in claim 1 in which said means for limiting radiation from said negative glow region passes radiation only from a zone that extends from the end surface of said cathode to the end of said negative glow toward said anode.

* * * * *